United States Patent
Carli

(10) Patent No.: US 7,335,200 B2
(45) Date of Patent: Feb. 26, 2008

(54) DYNAMIC INTERVERTEBRAL CONNECTION DEVICE WITH CONTROLLED MULTIDIRECTIONAL DEFLECTION

(75) Inventor: Olivier Carli, Geneva (CH)

(73) Assignee: Scient'X, Guyancourt (FR)

( * ) Notice: Subject to any disclaimer, the term of this patent is extended or adjusted under 35 U.S.C. 154(b) by 258 days.

(21) Appl. No.: 10/395,094

(22) Filed: Mar. 25, 2003

(65) Prior Publication Data

US 2004/0073215 A1    Apr. 15, 2004

(30) Foreign Application Priority Data

Oct. 14, 2002    (FR)    .................................. 02 12726

(51) Int. Cl.
 *A61B 17/70*    (2006.01)
(52) U.S. Cl. ........................................................ 606/61
(58) Field of Classification Search ................. 606/61; 623/17.11–17.16
See application file for complete search history.

(56) References Cited

U.S. PATENT DOCUMENTS

| | | | | |
|---|---|---|---|---|
| 4,932,975 A | * | 6/1990 | Main et al. | 623/17.12 |
| 5,375,823 A | * | 12/1994 | Navas | 623/17.15 |
| 5,413,602 A | * | 5/1995 | Metz-Stavenhagen | 623/17.15 |
| 5,480,442 A | * | 1/1996 | Bertagnoli | 623/17.14 |
| 6,241,730 B1 | * | 6/2001 | Alby | 606/61 |
| 6,267,764 B1 | | 7/2001 | Elberg | |
| 6,290,703 B1 | * | 9/2001 | Ganem | 606/73 |
| 6,440,169 B1 | * | 8/2002 | Elberg et al. | 623/17.16 |
| 6,770,095 B2 | * | 8/2004 | Grinberg et al. | 623/17.14 |
| 6,835,207 B2 | * | 12/2004 | Zacouto et al. | 623/17.12 |
| 2001/0047174 A1 | | 11/2001 | Donno et al. | |
| 2002/0095154 A1 | * | 7/2002 | Atkinson et al. | 606/61 |
| 2002/0151978 A1 | * | 10/2002 | Zacouto et al. | 623/17.12 |
| 2003/0055427 A1 | * | 3/2003 | Graf | 606/61 |
| 2004/0002708 A1 | * | 1/2004 | Ritland | 606/61 |
| 2004/0049189 A1 | * | 3/2004 | Le Couedic et al. | 606/61 |
| 2005/0049708 A1 | * | 3/2005 | Atkinson et al. | 623/17.16 |

FOREIGN PATENT DOCUMENTS

| | | |
|---|---|---|
| DM | 10004712 | 8/2001 |
| FR | 2814936 | 4/2002 |
| JP | 09108247 | 4/1997 |
| SU | 1102585 | 7/1984 |

* cited by examiner

*Primary Examiner*—Eduardo C. Robert
*Assistant Examiner*—Mary Hoffman
(74) *Attorney, Agent, or Firm*—Dennison, Schultz & MacDonald

(57) ABSTRACT

An osteosynthesis device having an elastically deformable connection system including a deformable connection member wherein a in a sagittal plane, determined stiffness for exerting in a return force on flexion-extension movements between the fixing portions, and in a frontal plane perpendicular to the sagittal plane, determined stiffness for exerting return force on lateral inflexion movements between the fixing portions.

11 Claims, 4 Drawing Sheets

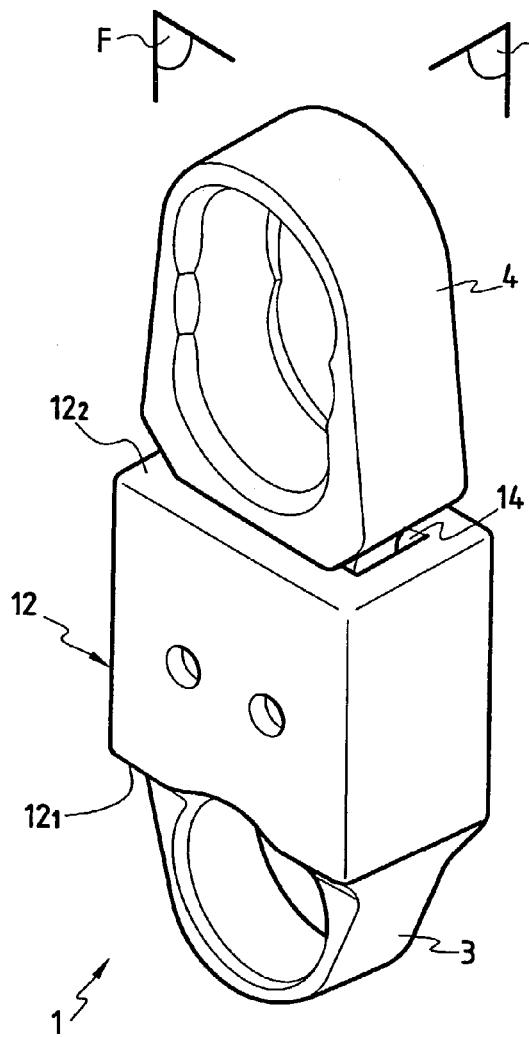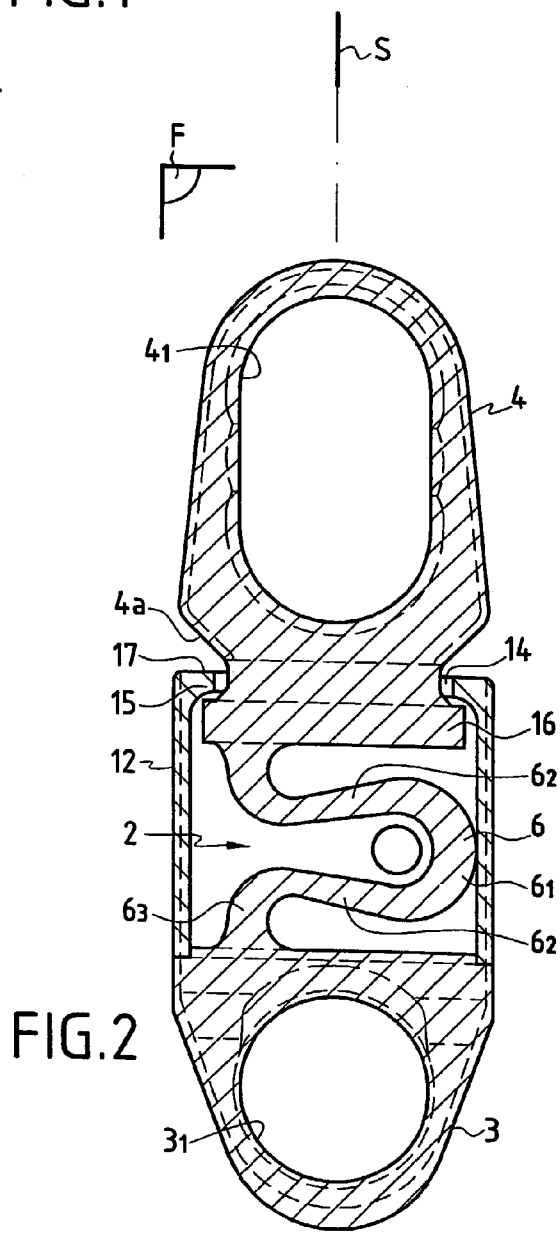

DYNAMIC INTERVERTEBRAL CONNECTION DEVICE WITH CONTROLLED MULTIDIRECTIONAL DEFLECTION

The present invention relates to the field of osteosynthesis devices intended in particular for treating defects and pathological states of the vertebral column or of vertebrae.

More particularly, the invention relates to a device for intervertebral stabilization serving to maintain at least two vertebrae in a suitable relative position in order to correct a patient's compacting of the vertebrae, scoloisis, lordosis, kyphosis, or intervertebral instability, for example.

BACKGROUND OF THE INVENTION

In the field of application concerning osteosynthesis of the spine, there exist numerous osteosynthesis devices, each comprising a connection system connected at either end to fixing portions suitable for being fixed to vertebrae via bone anchoring elements.

A first category of osteosynthesis devices are known which comprise a rigid connection connected at opposite ends to portions for fixing to the vertebrae. Such a rigid stabilization device leads to mechanical stresses being shifted to intervertebral joints adjacent to the joints that have been stabilized.

In order to remedy that problem, a second category of osteosynthesis device is known comprising an elastically deformable connection system connected at opposite ends to portions for fixing to the vertebrae. In general, such a "dynamic" intervertebral stabilization device has a spring or damper type system suitable for withstanding elastically any axial elongation or compression. Such a stabilization device is capable of damping both compression movement and traction movement, thereby allowing vertebral segments to move in physiological manner. Certain known devices are also adapted to damp flexion-extension movements in the antero-posterior plane and also lateral flexing movements.

Nevertheless, known prior solutions are not of simple design and they generally present relatively large bulk which makes it particularly difficult to place such a device in a non-stressed position.

OBJECT AND SUMMARY OF THE INVENTION

The object of the invention is thus to propose an intervertebral connection device designed to damp and control compression-traction, flexion-extension, and lateral inflexion movements while being compact and remaining simple in design.

To achieve such an object, the invention provides an osteosynthesis device for the vertebral column, the device comprising at least one elastically deformable connection system connected at opposite ends to at least first and second fixing portions suitable for being fixed to vertebrae by means of bone anchoring elements.

According to the invention, the elastically deformable connection system comprises:

a deformable connection member presenting:
  in a "sagittal" plane, determined stiffness for exerting a return force on flexion-extension movements between the fixing portions;
  in a "frontal" plane perpendicular to the sagittal plane, determined stiffness for exerting a return force on lateral inflexion movements between the fixing portions, the stiffness of the deformable connection member in the frontal plane being less than its stiffness in the sagittal plane; and
  along an axis defined by the intersection between the sagittal and frontal planes, determined stiffness for exerting a return force on traction-compression movements between the fixing portions;
and means for limiting flexion-extension, traction-compression, and lateral inflexion movements between the fixing portions.

BRIEF DESCRIPTION OF THE DRAWINGS

Other characteristics appear from the following description made with reference to the accompanying drawings which show embodiments of the subject matter of the invention as non-limiting examples.

FIG. 1 is a perspective view of a first embodiment of an osteosynthesis device in accordance with the invention.

FIG. 2 is an elevation section view of an osteosynthesis device as shown in FIG. 1.

MORE DETAILED DESCRIPTION

Figure 3:
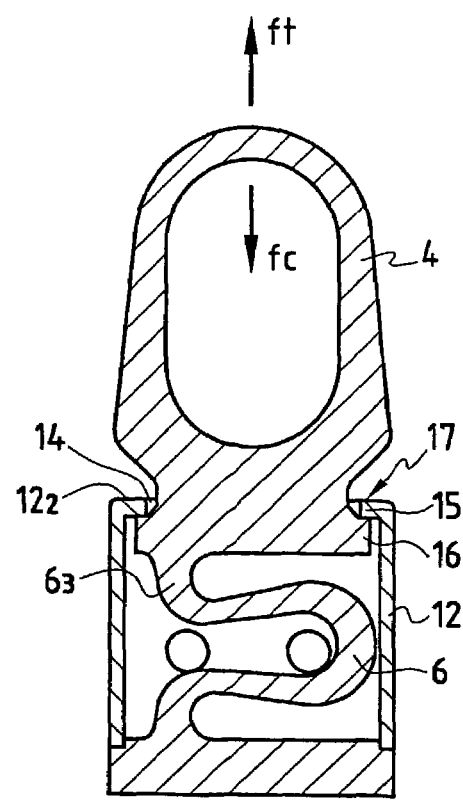
FIG. 3 is a fragmentary section view showing the osteosynthesis device shown in FIGS. 1 and 2 but in its traction position.

As can be seen more clearly from FIGS. 1 to 3, the invention provides an osteosynthesis device 1 for the vertebral column, the device comprising at least one elastically deformable connection system 2 connected at opposite ends to at least first and second fixing portions 3 and 4 adapted to be fixed to vertebrae via bone anchoring elements of any type such as pedicular screws or hooks.

In accordance with the invention, the elastically deformable connection system 2 comprises a deformable connection member 6 itself presenting:

in a plane S that is sagittal relative to anatomy, stiffness that is determined to exert a return force on flexion-extension movements between the fixing portions 3, 4;

in a "frontal" plane F perpendicular to the sagittal plane S, stiffness that is determined to exert a return force on left or right lateral inflexion movements of the fixing portions 3, 4; and along an axis where the sagittal plane S and the frontal plane F intersect, stiffness that is determined to exert a return force for traction-compression movements between the fixing portions 3, 4.

According to a characteristic of the invention, the stiffness of the deformable connection member in the frontal plane F is less than its stiffness in the sagittal plane S.

In the description above, the movements of the fixing portions 3 and 4 are resolved into individual types of movement. Naturally, once the osteosynthesis device 1 of the invention has been implanted, the movements of the spine that are imposed on the device comprise a combination of such individual movements.

In the embodiment shown in the drawings, the deformable connection member 6 is made by means of a flat element extending in a plane parallel to the frontal plane F. This flat element 6 also presents thickness extending in a plane parallel to the sagittal plane S. This flat element 6 which constitutes a spring is designed to exert a return force on flexion-extension, traction-compression, and lateral inflexion movements between the fixing portions 3, 4.

In a preferred variant embodiment, the flat element 6 presents a curved profile in the frontal plane F. Advantageously, the flat element 6 presents a profile in the frontal plane F that is curved so as to be lyre- or Ω-shaped. Thus, and as can be seen more clearly in FIG. 2, the flat element 6 presents a rounded core $6_1$ extended at opposite ends by respective branches $6_2$ which terminate in outwardly-directed curved end portions $6_3$. Each curved end portion $6_3$ is connected to a respective fixing portion 3, 4. In the embodiment shown, the flat element 6 has a right cross-section that is quadrangular in shape.

Figure 7:
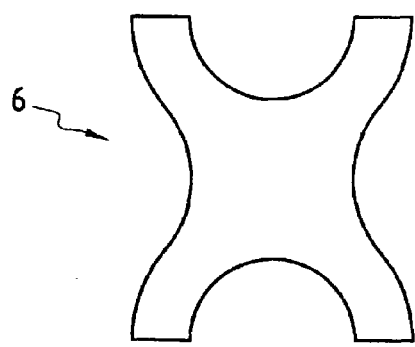
FIGS. 7 to 10 show various shapes suitable for embodying the deformable connection member forming a part of the osteosynthesis device in accordance with the invention.
Figure 8:
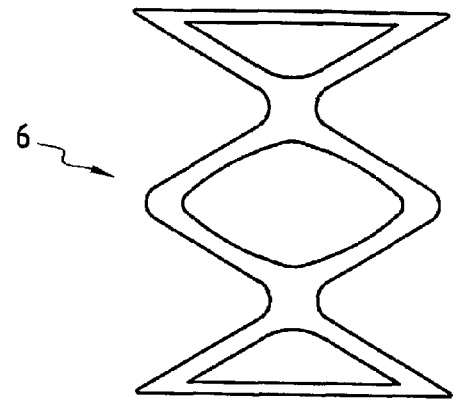
Figure 9:
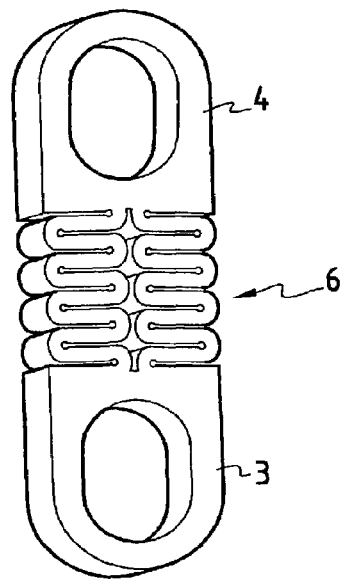
Figure 10:
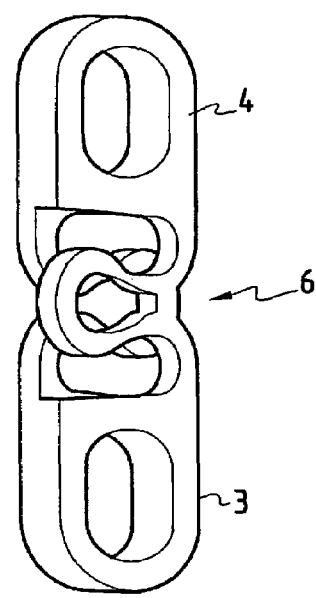

Naturally, the deformable connection member 6 may be made in a manner that differs from the variant shown in the drawings. Thus, for example, the deformable connection member 6 may be X-shaped (FIG. 7), may be a portion that is lozenge-shaped connected at opposite ends to respective triangular portions (FIG. 8), may be one or two successions of zigzag folds as shown in FIG. 9, or may comprise a pair of Ω-shapes mounted in opposite directions (FIG. 10).

In an aspect of the invention, implementing a deformable connection member of different shape and/or of different section provides the advantage of enabling said member to present a range of stiffnesses appropriate for patients of differing physiologies.

According to another advantageous characteristic of the invention, the elastically deformable connection system 2 has means for limiting flexion-extension, traction-compression, and lateral inflexion movements between the fixing portions 3 and 4. Such means serve to limit the amplitude of the movements that can be performed in traction-compression, in flexion-extension, or in lateral inflexion.

In a preferred embodiment, the means for limiting movements between the fixing portions 3 and 4 are constituted by abutment zones presented by a flat box 12 co-operating with corresponding zones of the flat element 6 which is mounted inside the box 12. As can be seen clearly from the figures, the flat box 12 is in the form of a rectangular parallelepiped having one of its faces, e.g. $12_1$, provided with the first fixing portion 3. The face $12_2$ of the box opposite from the face $12_1$ fitted with the first fixing portion 3, possesses a passage 14 for passing the second fixing portion 4. In other words, the passage 14 in the box is of a section which is greater than the section of the fixing portion 4 so as to enable the fixing portion 4 to move relative thereto.

The deformable connection member 6 is thus mounted inside the box 12 having the fixing portions 3 and 4 projecting from opposite ends thereof. Naturally, the box 12 is made of at least two assembled-together portions so as to enable the deformable connection member 6 to be mounted inside the box 12.

As described above, the box 12 is adapted to limit the amount of movement between the fixing portions 3 and 4.

As can be seen more clearly from FIG. 3, the box 12 has a shoulder 15 against which the flat element 6 comes to bear when a traction movement is exerted between the fixing portions 3 and 4, as represented by the arrow ft. In the example shown, the shoulder 15 is defined by the inside surface of the face $12_2$ of the box surrounding the passage 14. This shoulder 15 is designed to serve as an abutment for a collar 16 to which one of the curved portion $6_3$ of the flat element 6 is connected. Naturally, the right cross-section of the collar 16 is greater than that of the passage 14.

Similarly, the box 12 has an abutment zone 17 for limiting movement in compression between the fixing portions 3 and 4 as represented by arrow fc in the opposite direction to the traction arrow ft. In the example shown, the abutment zone 17 is formed by the outside surface of the face $12_2$ of the box surrounding the passage 14 and against which a bearing zone 4a of the fixing portion 4 comes into contact.

Figure 4:
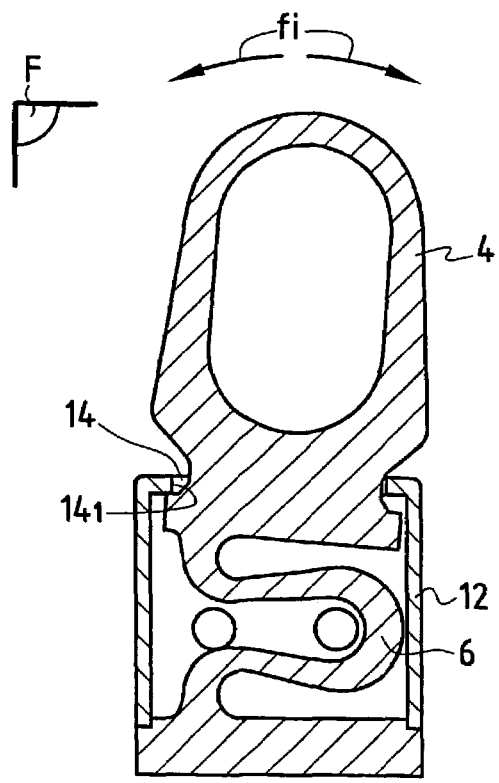
FIG. 4 is a fragmentary section view of the osteosynthesis device in its lateral inflexion position.

As can be seen more clearly in FIG. 4, the box 12 is adapted to limit natural inflexion movements between the fixing portions 3 and 4 taking place in the frontal plane F and represented by arrows fi. In the example shown, the deformable connection member 6 comes into abutment against the transverse edges $14_1$ defining the passage 14 during lateral inflexion movements.

Figure 5:
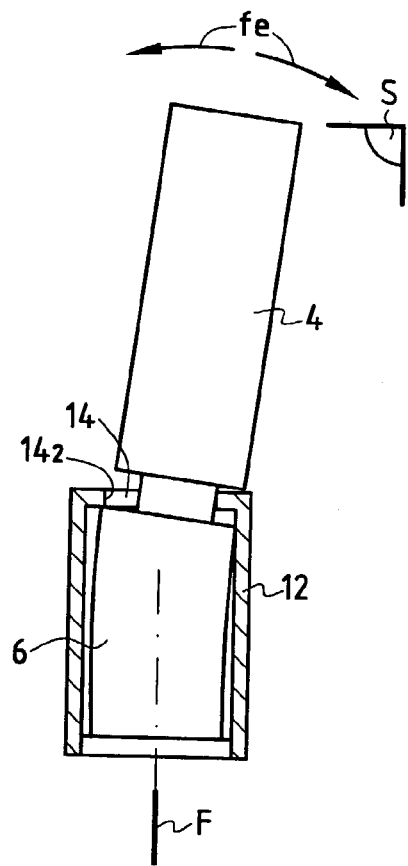
FIG. 5 is a fragmentary view showing an osteosynthesis device in its flexion position.

As can be seen more clearly in FIG. 5, the box 12 is adapted to limit flexion-extension movements between the fixing portions 3 and 4 taking place in the sagittal plane S and represented by arrows fe. In the example shown, the deformable connection member 6 comes into abutment against the longitudinal edges $14_2$ defining the passage 14 during flexion-extension movements.

The box 12, by means of its abutment-forming zones 15, 17, $14_1$, $14_2$ serves to limit and control traction-compression, lateral inflexion, and flexion-extension movements between the fixing portions 3 and 4. The osteosynthesis device of the invention serves to damp and control angular and axial relative movements so as to allow micro-movements to take place.

In an advantageous embodiment, the osteosynthesis device of the invention has means enabling the movements between the fixing portions 3 and 4 to be adjusted selectively. Thus, the adjustment means may selectively prevent either any flexion and/or inflexion movement, or any left or right inflexion movement, or any traction-compression movement. By way of example, these adjustment means may be implemented in the form of pegs placed inside the box 12 and acting as selective abutments for the deformable connection member 6, as explained above.

In a preferred embodiment, the fixing portions 3 and 4 when at rest, i.e. when no external stress is applied thereto, present an alignment offset in the sagittal plane S that is helpful in matching them to the angular shape of the spinal column.

In a preferred embodiment, the first fixing portion 3 is provided with a hole $3_1$ of circular right section for passing an anchoring element. Making a circular hole in one of the fixing portions 3 means that two devices of the invention are positioned symmetrically about an axis perpendicular to the frontal plane, which leads to devices of the invention operating in physiological manner. The second fixing portion 4 is provided with a hole $4_1$ for passing an anchoring element, which hole $4_1$ is oblong. The use of an oblong hole $4_1$ makes it possible to install an anchoring element in various different positions.

Figure 6:
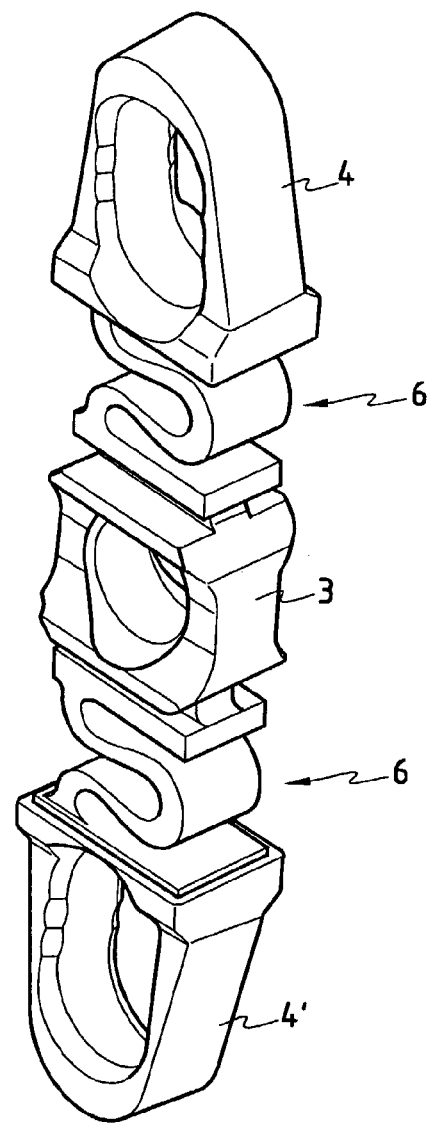
FIG. 6 shows another embodiment of an osteosynthesis device in accordance with the invention.

FIG. 6 shows another embodiment of an osteosynthesis device 1 in accordance with the invention implementing a second elastically deformable connection system 6 as described above. This second deformable connection system 6 is connected both to the first fixing portion 3 and to a third fixing portion 4'.

What is claimed is:

1. An osteosynthesis device for a vertebral column, the device comprising at least one elastically deformable connection system connected at opposite ends to at least first and second fixing portions suitable for being fixed to vertebrae by means of bone anchoring elements, wherein the elastically deformable connection system comprises:

a deformable connection member presenting:

in a "sagittal" plane, determined stiffness for exerting a return force on flexion-extension movements between the fixing portions;

in a "frontal" plane perpendicular to the sagittal plane, determined stiffness for exerting a return force on lateral inflexion movements between first and second fixing portions, the stiffness of the deformable connection member in the frontal plane being less than its stiffness in the sagittal plane; and along an axis defined by the intersection between the sagittal and frontal planes, determined stiffness for exerting a return force on traction-compression movements between the fixing portions;

and means for limiting flexion-extension, traction-compression, and lateral inflexion movements between the fixing portions, said means comprising a box having an inside surface; wherein the deformable connection member is mounted inside the box such that a space is defined between the inside surface of the box and the deformable connection member to allow movement of the deformable connection member relative to the box; and wherein the deformable connection member is implemented by means of a flat element extending in the frontal plane and presenting thickness in the sagittal plane, the flat element possessing at least a first end connected to the first fixing portion and a second end connected to the second fixing portion.

2. An osteosynthesis device according to claim 1, wherein the flat element presents a curved profile in the frontal plane, the curved profile preferably being lyre-shaped with its ends being connected to the fixing portions.

3. An osteosynthesis device according to claim 1, wherein the flat element presents a right cross-section that is quadrangular in shape.

4. An osteosynthesis device according to claim 1, wherein the flat element is disposed in the box provided with the first fixing portion which is connected to a first end of the flat element, the box having a passage for the second fixing portion which projects outside the box and which is connected to the second end of the flat element.

5. An osteosynthesis device according to claim 1, wherein the means for limiting flexion-extension, traction-compression, and lateral inflexion movements are constituted by abutment zones presented by the box and co-operating with zones of a flat element.

6. An osteosynthesis device according to claim 1, wherein the means for limiting flexion-extension movements are constituted by longitudinal edges defining a passage for the second fixing portion.

7. An osteosynthesis device according to claim 1, wherein the means for limiting traction-compression movements further comprises a shoulder provided on an interior surface of the box against which a collar made on the second end of a flat element comes into abutment.

8. An osteosynthesis device according to claim 1, wherein the means for limiting lateral inflexion movements are constituted by transverse edges defining the passage for the second fixing portion.

9. An osteosynthesis device according to claim 1, wherein a first fixing portion is provided with a circular through hole for passing an anchoring element, and wherein a second fixing portion is provided with an oblong through hole for passing an anchoring element.

10. An osteosynthesis device according to claim 1, wherein the fixing portions present an alignment offset in the sagittal plane.

11. An osteosynthesis device according to claim 1, including means enabling movements between the fixing portions to be adjusted selectively.

* * * * *